(12) United States Patent
Konishi

(10) Patent No.: US 11,642,302 B2
(45) Date of Patent: May 9, 2023

(54) COSMETIC

(71) Applicant: SHIN-ETSU CHEMICAL CO., LTD., Tokyo (JP)

(72) Inventor: Masayuki Konishi, Tokyo (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 248 days.

(21) Appl. No.: 16/981,216

(22) PCT Filed: Feb. 28, 2019

(86) PCT No.: PCT/JP2019/007764
§ 371 (c)(1),
(2) Date: Sep. 15, 2020

(87) PCT Pub. No.: WO2019/176555
PCT Pub. Date: Sep. 19, 2019

(65) Prior Publication Data
US 2021/0022984 A1    Jan. 28, 2021

(30) Foreign Application Priority Data
Mar. 16, 2018 (JP) .............................. JP2018-049322

(51) Int. Cl.
*A61K 8/895* (2006.01)
*A61K 8/92* (2006.01)
*A61Q 1/02* (2006.01)

(52) U.S. Cl.
CPC ............... *A61K 8/895* (2013.01); *A61K 8/92* (2013.01); *A61Q 1/02* (2013.01)

(58) Field of Classification Search
CPC .......... A61K 8/895; A61K 8/92; A61K 8/585; A61K 8/891; A61Q 1/02
See application file for complete search history.

(56) References Cited

U.S. PATENT DOCUMENTS

| | | | |
|---|---|---|---|
| 2009/0232859 A1 | 9/2009 | Sakuta et al. | |
| 2011/0070180 A1* | 3/2011 | Ranade | A61K 8/8123 424/70.121 |
| 2011/0301247 A1 | 12/2011 | Hayakawa et al. | |
| 2013/0287824 A1* | 10/2013 | Inaba | A61K 8/891 424/401 |
| 2017/0049667 A1* | 2/2017 | Shimizu | A61Q 1/02 |
| 2017/0216154 A1* | 8/2017 | Sonoyama | A61Q 1/10 |
| 2018/0228717 A1 | 8/2018 | Kubota | |
| 2019/0046421 A1 | 2/2019 | Yamaki et al. | |
| 2019/0211156 A1 | 7/2019 | Akabane et al. | |

FOREIGN PATENT DOCUMENTS

| | | |
|---|---|---|
| EP | 2 863 995 B1 | 11/2020 |
| JP | 2-25411 A | 1/1990 |
| JP | 4-45155 A | 2/1992 |
| JP | 7-196449 A | 8/1995 |
| JP | 2000-53530 A | 2/2000 |
| JP | 2005-41795 A | 2/2005 |
| JP | 2007-291094 A | 11/2007 |
| JP | 2008-31045 A | 2/2008 |
| JP | 2013-227287 A | 11/2013 |
| JP | 2014-108934 A | 6/2014 |
| JP | 2015-520120 A | 7/2015 |
| JP | 6030257 B1 | 11/2016 |
| JP | 2017-2017 A | 1/2017 |
| JP | 2017-71602 A | 4/2017 |
| JP | 2017-186305 A | 10/2017 |
| JP | 2017-186312 A | 10/2017 |
| JP | 2018-9100 A | 1/2018 |
| JP | 6441528 B1 | 12/2018 |

OTHER PUBLICATIONS

Toda Tomoko et al. (JP 2005041795 A, using the PE2E Eng. Translation) (Year: 2005).*
(JP 6030257 B1, (Nov. 24, 2016) using the PE2E Eng. Translation). (Year: 2016).*
Japanese Office Action for Japanese Application No. 2020-505755, dated Jan. 25, 2022.
International Search Report for PCT/JP2019/007764 (PCT/ISA/210) dated May 28, 2019.
Written Opinion of the International Searching Authority for PCT/JP2019/007764 (PCT/ISA/237) dated May 28, 2019.
Extended European Search Report for European Application No. 19767747.9, dated Dec. 22, 2021.
Japanese Office Action for Japanese Application No. 2020-505755, dated Jul. 26, 2022, with an English translation.

* cited by examiner

*Primary Examiner* — Blessing M Fubara
(74) *Attorney, Agent, or Firm* — Birch, Stewart, Kolasch & Birch, LLP

(57) ABSTRACT

This cosmetic contains: (a) 30 mass % or less of a highly oil-absorbing powder; (b) a volatile oil solution; and (c) a nonvolatile oil solution having a kinematic viscosity at 25° C. of 5 to 100 mm$^2$/s. The mixture mass ratio represented by (a)/(c) is 0.37 to 2.0.

14 Claims, No Drawings

COSMETIC

TECHNICAL FIELD

The present invention relates to a cosmetic. In this invention, a composition for cosmetic use is referred to as a "cosmetic."

BACKGROUND ART

Long-lasting cosmetic effects have hitherto been sought in makeup cosmetics. There exists also a desire for cosmetics which, following application, do not adhere to clothing and cups; that is, cosmetics which have an excellent "transfer resistance" effect.

Art that includes a film-forming agent such as trimethylsiloxysilicic acid or a silicone-modified acrylic polymer in a cosmetic for the purpose of enhancing the durability of the cosmetic effects or the transfer resistance is known (Patent Document 1: JP-A H04-45155; Patent Document 2: JP-A H02-25411; Patent Document 3: JP-A H07-196449). However, in such art, a large amount of addition is required to obtain a sufficient cosmetic durability; moreover, the influence on the "touch" of the cosmetic has been large.

Art which prevents the secondary adhesion of colorants by separating a colorant-dispersed phase from a colorant-free phase is also known (Patent Document 4: JP-A 2000-053530; Patent Document 5: JP-A 2013-227287). However, such a form requires that a high-viscosity oil of low compatibility be included for the sake of separation, but the touch ends up being heavy, limiting use as a lipstick cosmetic. Art that uses a polyoxyalkylene-modified silicone to increase the durability of cosmetics with a film that forms following application of the cosmetic is also known (Patent Document 6: JP-A 2008-031045). However, the cosmetic itself thickens when an aqueous ingredient is included, and so it has been difficult to use this approach in, for example, emulsified cosmetics.

PRIOR ART DOCUMENTS

Patent Documents

Patent Document 1: JP-A H04-45155
Patent Document 2: JP-A H02-25411
Patent Document 3: JP-A H07-196449
Patent Document 4: JP-A 2000-053530
Patent Document 5: JP-A 2013-227287
Patent Document 6: JP-A 2008-031045

SUMMARY OF INVENTION

Technical Problem

In light of the above circumstances, an object of this invention is to provide a cosmetic which has an excellent transfer resistance, durability, feel on use, ease of application and finish.

Solution to Problem

The inventor has conducted extensive investigations in order to achieve this object, discovering as a result that a highly oil-absorbent powder, by absorbing a volatile oil, is able to achieve a dry, silky feel on use and smoothness on application; and that, following application of the cosmetic, the volatile oil vaporizes and the highly oil-absorbent powder absorbs nonvolatile oils, resulting in less nonvolatile oil on the surface of powders such as color pigments having a low oil absorption, thus preventing such powders from adhering to clothing, etc., and also absorbs nonvolatile oils from foundation applied on top and from sebum, so that durability is obtained and there is no lingering powderiness, thus affording a natural finish. This discovery ultimately led to the present invention.

Accordingly, the present invention provides the following cosmetic.

1. A cosmetic which includes (a) a highly oil-absorbent powder having an oil absorption of at least 50 mL/100 g, (b) a volatile oil and (c) a nonvolatile oil having a kinematic viscosity at 25° C. of from 5 to 100 mm$^2$/s, wherein the weight ratio in which components (a) and (c) are included, expressed as (a)/(c), is from 0.37 to 2.0.
2. The cosmetic of 1 above, wherein the oil absorption of component (a) is at least 70 mL/100 g.
3. The cosmetic of 1 or 2 above, wherein component (a) is one or more selected from the group consisting of, as defined in the International Nomenclature of Cosmetic Ingredient (INCI): (vinyl dimethicone/methicone silsesquioxane) crosspolymer, (diphenyl dimethicone/vinyl diphenyl dimethicone/silsesquioxane) crosspolymer, polysilicone-22 and polysilicone-1 crosspolymer.
4. The cosmetic of any of 1 to 3 above, further including (d) a powder other than component (a).
5. The cosmetic of 4 above, wherein the combined amount of components (a) and (d) is not more than 45 wt % of the cosmetic.
6. The cosmetic of 4 or 5 above, wherein the weight ratio in which components (a) and (d) are included, expressed as (a)/(d), is at least 0.3.
7. The cosmetic of any of 1 to 6 above, wherein component (c) is a nonvolatile oil that has a kinematic viscosity at 25° C. of from 5 to 100 mm$^2$/s and is selected from the group consisting of silicone oils, low-polarity oils, high-polarity oils and ultraviolet absorbers.
8. The cosmetic of 7 above, wherein component (c) is selected from silicone oils having a kinematic viscosity at 25° C. of from 5 to 100 mm$^2$/s and high-polarity oils having an inorganic-organic balance (IOB) of from 0.1 to 0.6 and a kinematic viscosity at 25° C. of at least 5 mm$^2$/s and less than 20 mm$^2$/s.
9. The cosmetic of any of 1 to 6 above, wherein component (a) is polysilicone-22 and component (c) is a nonvolatile oil that has a kinematic viscosity at 25° C. of from 5 to 100 mm$^2$/s and is selected from the group consisting of silicone oils, low-polarity oils and high-polarity oils.
10. The cosmetic of any of 1 to 6 above, wherein component (a) is selected from the group consisting of (vinyl dimethicone/methicone silsesquioxane) crosspolymer and polysilicone-1 crosspolymer, and component (c) is selected from silicone oils that have a kinematic viscosity at 25° C. of from 5 to 100 mm$^2$/s and high-polarity oils that have an IOB of from 0.1 to 0.6 and a kinematic viscosity at 25° C. of at least 5 mm$^2$/s and less than 20 mm$^2$/s.
11. The cosmetic of any of 1 to 6 above, wherein component (a) is (diphenyl dimethicone/vinyl diphenyl dimethicone/silsesquioxane) crosspolymer and component (c) is a nonvolatile oil that has a kinematic viscosity at 25° C. of from 5 to 100 mm$^2$/s and is selected from the group consisting of methylphenylpolysiloxane, high-polarity oils and ultraviolet absorbers.
12. The cosmetic of any of 1 to 11 above, further including (e) a water-soluble nonvolatile ingredient in an amount of less than 12 wt % of the cosmetic.

13. The cosmetic of any of 1 to 12 above, further including (f) a nonvolatile oil having a kinematic viscosity at 25° C. in excess of 100 mm²/s in an amount of less than 5 wt % of the cosmetic.
14. The cosmetic of any of 1 to 13 above which is a makeup cosmetic.

Advantageous Effects of Invention

The present invention enables cosmetics having an excellent transfer resistance, durability, feel on use, ease of application and finish to be provided.

DESCRIPTION OF EMBODIMENTS

The invention is described in detail below.
[Component (a)]
Component (a) of the invention is a highly oil-absorbent powder having an oil absorption of 50 mL/100 g or more. One type may be used alone or two or more may be used in suitable combination. In this invention, "highly oil-absorbent powder" refers to a powder having an oil absorption, as determined by a method of measurement wherein linseed oil in the test method of JIS K5101 is replaced with KF-56A (Shin-Etsu Chemical Co., Ltd.), of at least 50 mL/100 g (50 mL of oil absorbed per 100 g of powder), preferably at least 70 mL/100 g, more preferably at least 100 mL/100 g, and even more preferably at least 120 mL/100 g. With a powder having an oil absorption of less than 50 mL/100 g, sufficient transfer resistance and durability are not obtained and the cosmetic may be heavy to the touch. There is no particular upper limit in the oil absorption, although this can be set to 200 mL/100 g or less.

In terms of the feel on use of the cosmetic, the highly oil-absorbent powder is preferably a spherical powder. "Spherical powder" refers to a powder in which the particles are spherical in shape and have sphere-approximating diameters; it may be composed of spherical particles having surface irregularities. Specifically, a spherical powder in which the spherical particles have a breadth/length ratio of 1.5 or less is preferred, one in which this is 1.2 or less is more preferred, and one in which this is 1.1 or less is even more preferred. A composite spherical powder in which these spherical particles are coated with a differing spherical powder is preferred. The shape of the powder can be ascertained by examination with an optical microscope or an electron microscope. The average particle size of the powder is not particularly limited, although for a dry, silky feel and good smoothness when included in the cosmetic, the volume mean particle diameter (cumulative $D_{50}$ (median diameter)) by the Coulter counter method is preferably from 0.1 to 100 µm, more preferably from 0.5 to 40 µm, and even more preferably from 1 to 15 µm.

Examples of spherical powders include crosslinked silicone powders (i.e., so-called silicone rubber powders composed of organopolysiloxane having a structure in which chains of repeating diorganosiloxane units are crosslinked), acrylic polymers such as methyl methacrylate crosspolymer, non-crosslinked cellulose and porous silica. Specific examples of highly oil-absorbent crosslinked silicone powders include (dimethicone/vinyl dimethicone) crosspolymer (International Nomenclature of Cosmetic Ingredients (INCI) name). These powders are commercially available as silicone oil-containing swollen powders, examples of which include those sold under the trade names KMP-598 and KSG-016F (both from Shin-Etsu Chemical Co., Ltd.). One or more of these powders may be used.

From the standpoint of improving the feel on use and the dispersibility in cosmetics, component (a) is preferably a composite spherical powder. Of these, from the standpoint of the touch-improving effects such as preventing stickiness and the wrinkle, pore and other shape-correcting effects, silicone resin-coated silicone rubber powders are preferred. Specific examples of highly oil-absorbent silicone resin-coated silicone rubber powders (silicone composite spherical powders) include, as defined in the INCI: (vinyl dimethicone/methicone silsesquioxane) crosspolymer, (diphenyl dimethicone/vinyl diphenyl dimethicone/silsesquioxane) crosspolymer, polysilicone-22 and polysilicone-1 crosspolymer. These are commercially available under such trade names as KSP-100, 101, 102, 105, 300, 411 and 441 (all from Shin-Etsu Chemical Co., Ltd.). Preferred examples among these include (vinyl dimethicone/methicone silsesquioxane) crosspolymers [KSP-100, 101, 102] and polysilicone-1 crosspolymer [KSP-411] which have high oil absorptions for silicone oils, diphenyl dimethicone/vinyl diphenyl dimethicone/silsesquioxane) crosspolymer [KSP-300] which has a high oil absorbency with respect to ultraviolet absorbers, and polysilicone-22 [KSP-441] which has a high oil-absorbing ability with respect to a broad range of oils. Of these, polysilicone-22 [KSP-441], which has an excellent cosmetic durability-enhancing effect, is preferred.

Highly oil-absorbent powders other than the above, such as color pigments, inorganic powders, metal powders, organic powders and inorganic/organic composite powders, may also be used as the highly oil-absorbent powder (a).

Color Pigments

The color pigments are not particularly limited, provided they are pigments that are typically used for the purpose of coloring preparations. For example, any of the following may be used: red iron oxide, yellow iron oxide, white titanium dioxide, black iron oxide, bengala, ultramarine, Prussian blue, manganese violet, cobalt violet, chromium hydroxide, chromium oxide, cobalt oxide, cobalt titanate, iron oxide-doped titanium dioxide, iron titanate, fired (titanium/titanium dioxide), lithium cobalt titanate and cobalt titanium; inorganic brown pigments such as titanium nitride, iron hydroxide and γ-iron oxide; inorganic yellow pigments such as ocher; and organic pigments such as lakes of coal-tar colorants and lakes of natural colorants. The pigment shape may be any shape, such as a spherical, substantially spherical, rod-like, spindle-like, petal-like, reed-like or amorphous shape. So long as it is possible to impart color to the preparation, the geometrical form is not particularly limited.

Inorganic Powders

Examples of inorganic powders include fine particles composed of zirconium oxide, cerium oxide, magnesium oxide, barium sulfate, calcium sulfate, magnesium sulfate, calcium carbonate, magnesium carbonate, talc, cleaved talc, mica, kaolin, sericite, muscovite, synthetic mica, phlogopite, lepidolite, biotite, lithia mica, silicic acid, silicon dioxide, fumed silica, anhydrous silicon dioxide, aluminum silicate, magnesium silicate, aluminum magnesium silicate, calcium silicate, barium silicate, strontium silicate, metal salts of tungstic acid, hydroxyapatite, vermiculite, hydrite, bentonite, montmorillonite, hectorite, zeolite, ceramic, calcium diphosphate, alumina, aluminum hydroxide, boron nitride and glass. Examples of inorganic colored pearlescent pigments include pearlescent pigments such as titanium dioxide-coated mica, bismuth oxychloride, titanium dioxide-coated bismuth oxychloride, titanium dioxide-coated talc, fish scale guanine and titanium dioxide-coated colored mica.

Metal Powders

Examples of metal powders include metal fine particles made of aluminum, copper, stainless steel, silver or the like.

Organic Powders

Examples of organic powders include powders made of silicone, polyamide, polyacrylic acids/acrylic acid ester, polyester, polyethylene, polypropylene, polystyrene, styrene/acrylic acid copolymer, divinylbenzene/styrene copolymer, polyurethane, vinyl resin, urea resin, melamine resin, benzoguanamine, polymethyl benzoguanamine, tetrafluoroethylene, polymethyl methacrylate, cellulose, silk, nylon, phenolic resins, epoxy resin or polycarbonate. Metal soaps can also be mentioned, specific examples of which include powders made of zinc stearate, aluminum stearate, calcium stearate, magnesium stearate, zinc myristate, magnesium myristate, zinc cetyl phosphate, calcium cetyl phosphate and zinc sodium cetyl phosphate. Additionally, organic colors can be mentioned as well, specific examples of which include coal-tar colorants such as Red No. 3, Red No. 104, Red No. 106, Red No. 201, Red No. 202, Red No. 204, Red No. 205, Red No. 220, Red No. 226, Red No. 227, Red No. 228, Red No. 230, Red No. 401, Red No. 505, Yellow No. 4, Yellow No. 5, Yellow No. 202, Yellow No. 203, Yellow No. 204, Yellow No. 401, Blue No. 1, Blue No. 2, Blue No. 201, Blue No. 404, Green No. 3, Green No. 201, Green No. 204, Green No. 205, Orange No. 201, Orange No. 203, Orange No. 204, Orange No. 206 and Orange No. 207; and natural colorants such as carminic acid, laccaic acid, carthamin, brazilin and crocin.

Inorganic/Organic Composite Powders

Inorganic/organic composite powders are exemplified by composite powders in which the surface of an inorganic powder has been coated with an organic powder by a publicly known and used method.

The above-mentioned powders may also be used in a form in which the particles have been surface treated. The surface treatment is preferably one that can impart hydrophobicity so that the water resistance of the preparation is not lost, and is not particularly limited provided that hydrophobicity can be imparted. Exemplary surface treatments include silicone treatments, waxes, paraffins, organofluorine compounds such as perfluoroalkylphosphates, surfactants, amino acids such as N-acylglutamic acid, and metal soaps such as aluminum stearate and magnesium myristate. More preferred silicone treatments include silanes or silylating agents such as caprylylsilane (AES-3083, from Shin-Etsu Chemical Co., Ltd.) and trimethoxysilyl dimethicone; silicone oils such as dimethylsilicone (KF-96A Series, from Shin-Etsu Chemical Co., Ltd.), methylhydrogen-type polysiloxanes (e.g., KF-99P and KF-9901, from Shin-Etsu Chemical Co., Ltd.), and silicone-branched silicone treatments (e.g., KF-9908 and KF-9909, from Shin-Etsu Chemical Co., Ltd.); and silicone acrylates (KP-574, KP-541, from Shin-Etsu Chemical Co., Ltd.). In addition, the surface hydrophobizing treatment may be of one type used alone or of two or more types used in combination. Specific examples of dispersions that contain hydrophobized microparticulate titanium dioxide or hydrophobized microparticulate zinc oxide include SPD-T5, T6, TSL, Z5, Z6 and Z5L, all from Shin-Etsu Chemical Co., Ltd.

The content of component (a) is 30 wt % or less, preferably from 0.1 to 30 wt %, more preferably from 5 to 25 wt %, and even more preferably from 10 to 20 wt %, of the cosmetic. At a component (a) content greater than 30 wt %, excessive dryness is felt, an unnatural finish results, and the finish that is desired cannot obtained.

[Component (b)]

Component (b) of the invention is a volatile oil. One volatile oil may be used alone or two or more may be used in suitable combination. Including component (b) enhances the transfer resistance. In this invention, "volatile oil" refers to an oil having a boiling point of 250° C. or less. Specific examples include dimethylpolysiloxanes having a boiling point of 250° C. or less (e.g., KF-96L-1cs, KF-96L-1.5cs, KF-96L-2cs, from Shin-Etsu Chemical Co., Ltd.), octamethyltetrasiloxane (D4), decamethylcyclopentasiloxane (KF-995 (D5), from Shin-Etsu Chemical Co., Ltd.), dodecamethylhexasiloxane (D6), tristrimethylsiloxymethylsilane (TMF-1.5, from Shin-Etsu Chemical Co., Ltd.), caprylyl methicone, light isoparaffin, undecane and isododecane.

The content of component (b) is preferably from 5 to 80 wt %, more preferably from 6 to 75 wt %, even more preferably from 8 to 60 wt %, and still more preferably from 10 to 50 wt %, of the cosmetic. At less than 5 wt %, a light feel on use may not be obtained; at more than 80 wt %, an excess dryness may be felt.

The weight ratio in which component (a) and component (b) are included in the cosmetic, expressed as (a)/(b), is preferably 1.0 or less, more preferably 0.7 or less, even more preferably 0.4 or less, and most preferably 0.2 or less. At a weight ratio greater than 1.0, the cosmetic may have a heavy feel on use and, in the case of emulsified compositions, the emulsified state may worsen. Although this weight ratio has no particular lower limit, the lower limit may be set to 0.1.

[Component (c)]

Component (c) of this invention is a nonvolatile oil that has a kinematic viscosity at 25° C. of from 5 to 100 mm$^2$/s. So long as it is an ingredient which can be included in conventional cosmetics, it is not particularly limited. One such nonvolatile oil may be used alone or two or more may be used in suitable combination. The kinematic viscosity at 25° C. of component (c) is from 5 to 100 mm$^2$/s (cSt, sometimes written as "cs"), preferably from 5 to 50 mm$^2$/s, and more preferably from 5 to 30 mm$^2$/s. With a high loading of nonvolatile oil having a kinematic viscosity of less than 5 mm$^2$/s, irritation may be sensed; with a high loading of nonvolatile oil having a kinematic viscosity in excess of 100 mm$^2$/s, the transfer resistance and durability may decrease. In this invention, the kinematic viscosity is a value measured at 25° C. with an Ostwald viscometer. As used herein, "nonvolatile" refers to oils which do not fit the above description of a volatile oil.

Component (c) is exemplified by nonvolatile oils that have a kinematic viscosity at 25° C. of from 5 to 100 mm$^2$/s and are selected from the group consisting of silicone oils, low-polarity oils, high-polarity oils and ultraviolet absorbers. One type may be used alone or two or more may be used in suitable combination.

Silicone Oils

The silicone oils are not particularly limited, provided that they are ingredients which can be included in conventional cosmetics. Specific examples include methylphenylpolysiloxanes such as dimethylpolysiloxane, diphenyl dimethicone (INCI name) and diphenylsiloxy phenyl trimethicone (INCI name), methylhexylpolysiloxane, methylhydrogenpolysiloxane and dimethylsiloxane/methylphenylsiloxane copolymers. Of these, low-viscosity silicones that enable a light feel on use to be obtained (commercial products include KF-96A-6cs, 10cs, 20cs and 100cs from Shin-Etsu Chemical Co., Ltd.), and methylphenylpolysiloxanes (available as the commercial product KF-56A from Shin-Etsu Chemical Co., Ltd.) such as diphenylsiloxy phenyl trimethicone (INCI name) that are used for the purpose of increasing compatibility with other oils and for luster are preferred. These silicone oils may be of one type used alone or two or more may be used together. From the standpoint of the oil absorbency to highly oil-absorbent powders, obtaining a light feel on use and water resistance, it is preferable to use a silicone oil as component (c).

Low-Polarity Oils

In this invention, "low-polarity oil" refers to an oil having an inorganic-organic balance (IOB) of less than 0.1. The IOB value is the ratio of inorganicity to organicity in the Organic Conceptual Diagram; that is, it can be calculated as "inorganicity/organicity" (for details on the Organic Conceptual Diagram, refer to Yūki gainen-zu-Kiso to ōyō-[Organic Conceptual Diagram—Fundamentals and Applications—] by Yoshio Kōda (Sankyo Shuppan, 1984)). Specific examples of low-polarity oils include hydrocarbon oils such as squalane, mineral oils, hydrogenated polyisobutene and jojoba oil.

High-Polarity Oils

The high-polarity oils of the present invention are exemplified by esters. Examples include esters having an IOB of from 0.1 to 0.4 and a kinematic viscosity at 25° C. of from 20 to 100 mm$^2$/s, and (2) low-viscosity oils having an IOB of from 0.1 to 0.6 and a kinematic viscosity at 25° C. of less than 20 mm$^2$/s.

(1) Examples of high-polarity oils having an IOB of 0.1 to 0.4 and a kinematic viscosity at 25° C. of 20 to 100 mm$^2$/s include the following which are indicated by their INCI names: triethylhexanoin, glyceryl (caprylate/caprate) and octyldodecyl lactate.

(2) Examples of low-viscosity high-polarity oils having an IOB of 0.1 to 0.6 and a kinematic viscosity at 25° C. of at least 5 mm$^2$/s but less than 20 mm$^2$/s include isodecyl isononanoate, isononyl isononanoate, cetyl ethylhexanoate, ethylhexyl palmitate, neopentyl glycol diethylhexanoate, isopropyl myristate, dicaprylyl carbonate and $C_{12-15}$ alkyl benzoates. From the standpoint of the oil absorbency to highly oil-absorbent powders, light feel on use and adhesion to the skin, it is preferable to use the above low-viscosity high-polarity oils.

Ultraviolet Absorbers

Specific examples of ultraviolet absorbers having a kinematic viscosity at 25° C. of 5 to 100 mm$^2$/s include, indicated by their INCI names: ethylhexyl methoxycinnamate and ethylhexyl salicylate.

The content of component (c) in the cosmetic is preferably not more than 15 wt %, more preferably not more than 10 wt %, even more preferably not more than 8 wt %, and still more preferably not more than 6 wt %. When the content exceeds 15 wt %, a sufficient transfer resistance and durability may not be obtained. For good adhesion of the cosmetic and to avoid a sensation of excessive dryness, including at least 3 wt % is preferred.

The weight ratio in which components (a) and (c) are included, expressed as (a)/(c), is from 0.37 to 2.0, preferably from 0.50 to 1.9, more preferably from 0.59 to 1.8, even more preferably from 0.7 to 1.7, and still more preferably from 1.00 to 1.5. At a weight ratio below 0.37, a sufficient durability is not obtained; at more than 2.0, an excessive dryness is felt and a good finish is not obtained.

By selecting in particular a component (a) which absorbs component (c) well, the advantageous effects can be clearly manifested. Examples of combinations thereof include the three combinations shown below. Any one of these combinations may be used alone, or two or more may be suitably used together.

In cases where component (a) is polysilicone-2 and component (c) is a nonvolatile oil that has a kinematic viscosity at 25° C. of from 5 to 100 mm$^2$/s and is selected from the group consisting of silicone oils, low-polarity oils and high-polarity oils, a higher transfer resistance and durability can be obtained.

In cases where component (a) is selected from (vinyl dimethicone/methicone silsesquioxane) crosspolymer and polysilicone-1 crosspolymer and component (c) is a nonvolatile oil selected from silicone oils having a kinematic viscosity at 25° C. of from 5 to 100 mm$^2$/s and high-polarity oils having an IOB of 0.1 to 0.6 and a kinematic viscosity at 25° C. of less than 20 mm$^2$/s, a higher transfer resistance and durability can be obtained.

In cases where component (a) is (diphenyl dimethicone/vinyl diphenyl dimethicone/silsesquioxane) crosspolymer and component (c) is a nonvolatile oil having a kinematic viscosity at 25° C. of 5 to 100 mm$^2$/s that is selected from methylphenylpolysiloxane, high-polarity oils and ultraviolet absorbers, a higher transfer resistance and durability can be obtained.

[Component (d)]

The cosmetic of the invention may include (d) a powder other than component (a); that is, a powder having an oil absorption of less than 50 mL/100 g. One type of component (d) may be used alone or two or more may be used in suitable combination. Examples include the color pigments, inorganic powders, metal powders, organic powders and inorganic/organic composite powders mentioned in (a) above which have oil absorptions of less than 50 mL/100 g.

Specific examples of component (d) include the following commercial products: the KTP-09 series (KTP-09W, 09R, 09Y, 09B) and KMP-590 and 591, all from Shin-Etsu Chemical Co., Ltd. These are color pigments and silicone resin particles (polyorganosilsesquioxane resin particles having a three-dimensional network structure) that have been surface treated.

When component (d) is included, the content thereof within the cosmetic preparation is preferably from 0.1 to 35 wt %, and more preferably from 1.0 to 25 wt %.

When component (d) is included, the weight ratio of component (a) to component (d), expressed as (a)/(d), is preferably at least 0.3, more preferably at least 0.5, even more preferably at least 0.7, and still more preferably at least 0.9. The upper limit, although not particularly limited, is preferably set to 3.0 for reasons having to do with the feel on use. The combined weight ratio of components (a) and (d) is preferably not more than 45 wt %, more preferably not more than 40 wt %, and even more preferably not more than 30 wt %, of the cosmetic preparation. The lower limit, although not particularly limited, may be set to 0.1 wt %.

[Component (e)]

The cosmetic of the invention may include (e) a water-soluble nonvolatile ingredient which is not particularly limited, provided that it can be included in conventional cosmetics. One such ingredient may be used alone or two or more may be used in suitable combination. Such ingredients are exemplified by compounds which have two or more hydroxyl groups on the molecule, can be mixed with water, and are not volatile at room temperature. Specific examples include sugar alcohols such as sorbitol, maltose and xylitol; polyhydric alcohols such as butylene glycol, dibutylene glycol, propylene glycol, pentylene glycol, decanediol, octanediol, hexanediol, erythritol, glycerol, diglycerol and polyethylene glycol; glucose, glyceryl glucoside, betaine, hyaluronic acid, chondroitin sulfate, pyrrolidone carboxylate, polyoxyethylene methyl glucoside and polyoxypropylene methyl glucoside. Of these, ingredients that are liquid at 25° C., such as butylene glycol, dibutylene glycol, propylene glycol, pentylene glycol, decanediol, octanediol, hexanediol, glycerin, diglycerol and polyethylene glycol having an average molecular weight below 1,000, are preferred.

The content of component (e) may be 0 wt %. However, when component (e) is included, the component (e) content in the cosmetic is preferably not more than 12 wt %, more preferably not more than 8 wt %, and even more preferably not more than 5 wt %. From the standpoint of transfer resistance, it is preferable to not include this component. However, in the case of an emulsified composition, including at least 3 wt % is preferred for improving the stability.

[Component (f)]

The cosmetic of the invention includes as an essential ingredient (c) a nonvolatile oil having a kinematic viscosity at 25° C. of from 5 to 100 mm$^2$/s, but it may also include (f) a nonvolatile oil having a kinematic viscosity at 25° C. that is greater than 100 mm$^2$/s. From the standpoint of transfer resistance and durability, it is preferable for the included amount of nonvolatile oil having a kinematic viscosity at 25° C. that is greater than 100 mm$^2$/s, especially an oil that is paste-like at 25° C., to be low. Examples of nonvolatile oils include those mentioned above in connection with component (c). Examples of oils that are paste-like at 25° C. include petrolatum and lanolin.

The content of component (f) may be 0 wt %. In cases where component (f) is included, the component (f) content is preferably less than 5 wt %, and more preferably 3 wt % or less. It is even more preferable for none to be included.

[Other Optional Ingredients]

Aside from the above ingredients, various optional ingredients that are used in conventional cosmetics may be included in the inventive cosmetic within ranges that do not detract from the advantageous effects of the invention. Examples of such ingredients include (1) surfactants, (2) crosslinked organopolysiloxanes, (3) film-forming agents, (4) aqueous ingredients other than component (e), (5) ultraviolet absorbers other than component (c), (6) waxes and (7) other additives. One of these may be used alone or two or more may be used in suitable combination.

(1) Surfactants

The surfactants are exemplified by nonionic, anionic, cationic and amphoteric surfactants, and are not particularly limited. Use can be made of any surfactant used in conventional cosmetics. One surfactant may be used alone or two or more may be used in suitable combination. Of these surfactants, partially crosslinked polyether-modified silicones, partially crosslinked polyglycerol-modified silicones, linear or branched polyoxyethylene-modified organopolysiloxanes, linear or branched polyoxyethylene-polyoxypropylene-modified organopolysiloxanes, linear or branched polyoxyethylene/alkyl co-modified organopolysiloxanes, linear or branched polyoxyethylene-polyoxypropylene/alkyl co-modified organopolysiloxanes, linear or branched polyglycerol-modified organopolysiloxanes and linear or branched polyglycerol/alkyl co-modified organopolysiloxanes are preferred. Specific examples include KSG-210, 240, 310, 320, 330, 340, 320Z, 350Z, 710, 810, 820, 830, 840, 820Z, 850Z, KF-6011, 6013, 6017, 6043, 6028, 6038, 6048, 6100, 6104, 6105, 6106 and KP-578 from Shin-Etsu Chemical Co., Ltd. When a surfactant is included, the content thereof is preferably from 0.01 to 15% of the cosmetic preparation.

(2) Crosslinked Organopolysiloxanes

The crosslinked organopolysiloxanes are not particularly limited, provided they are ones that are used in conventional cosmetics. One crosslinked organopolysiloxane may be used alone or two or more may be used in suitable combination. These crosslinked organopolysiloxanes are compounds without polyether or polyglycerol moieties in the molecular structure, and are elastomers which, by swelling with an oil, have structural viscosity. Examples include (dimethicone/vinyl dimethicone) crosspolymer, (dimethicone/phenyl vinyl dimethicone) crosspolymer, (vinyl dimethicone/lauryl dimethicone) crosspolymer and (lauryl polydimethylsiloxyethyl dimethicone/bis-vinyl dimethicone) crosspolymer. These are commercially available as swollen products containing an oil that is liquid at room temperature, examples of which include KSG-15, 1510, 16, 1610, 18A, 19, 41A, 42A, 43, 44, 042Z, 045Z and 048Z from Shin-Etsu Chemical Co., Ltd. When a crosslinked organopolysiloxane is included, the amount thereof is preferably from 0.01 to 30% of the cosmetic.

(3) Film-Forming Agents

The film-forming agent is not particularly limited, provided it is an ingredient that can be included in conventional cosmetics. Specific examples include latexes of polyvinyl alcohol, polyvinyl pyrrolidone, polyvinyl acetate and polyalkyl acrylates; cellulose derivatives such as dextrin, alkyl celluloses and nitrocellulose; siliconized polysaccharide compounds such as tri(trimethylsiloxy)silylpropylcarbamic acid pullulan, acrylate-silicone graft copolymers such as (alkyl acrylate/dimethicone) copolymers, silicone resins such as trimethylsiloxysilicic acid, silicone-modified polynorbornene, silicone-based resins such as fluorine-modified silicone resins, fluorocarbon resins, aromatic hydrocarbon resins, polymer emulsion resins, terpene resins, polybutenes, polyisoprenes, alkyd resins, polyvinyl pyrrolidone-modified polymers, rosin-modified resins and polyurethanes.

Of these, from the standpoint of water resistance, oil resistance and feeling on use, silicone-based film-forming agents are preferred. Examples of silicone-based film-forming agents that may be used include, but are not limited to, tri(trimethylsiloxy)silylpropylcarbamic acid pullulan (commercially available in solvent-dissolved forms as TSPL-30-D5 and ID from Shin-Etsu Chemical Co., Ltd.), (alkyl acrylate/dimethicone) copolymers (available in solvent-dissolved forms as KP-543, 545, 549, 550 and 545L from Shin-Etsu Chemical Co., Ltd.), trimethylsiloxysilicic acid (available in solvent-dissolved forms as KF-7312) and X-21-5250 from Shin-Etsu Chemical Co., Ltd.) and silicone-modified polynorbornene (available in a solvent-dissolved form as NBN-30-ID from Shin-Etsu Chemical Co., Ltd.). When a film-forming agent is included, the content thereof is preferably from 0.1 to 20% of the cosmetic.

(4) Aqueous Ingredients Other than Component (e)

Aqueous ingredients other than component (e) are not particularly limited, provided that they are ingredients which have volatility and can be included in conventional cosmetics. Examples include lower alcohols such as ethanol and isopropanol, water and the like. In cases where an aqueous ingredient is included, the content thereof within the cosmetic is preferably from 0.1 to 70 wt %.

(5) Ultraviolet Absorbers Other than Component (c)

Ultraviolet absorbers other than component (c) are not particularly limited, provided that they are ingredients which can be included in conventional cosmetics. Illustrative examples include homomenthyl salicylate, octocrylene, 4-tert-butyl-4'-methoxydibenzoyl methane, 4-(2-β-glucopyranosiloxy)propoxy-2-hydroxybenzophenone, hexyl 2-[4-(diethylamino)-2-hydroxybenzoyl]benzoate, dihydroxydimethoxybenzophenone, sodium dihydroxydimethoxybenzophenone disulfonate, dihydroxybenzophenone, dimethicodiethyl benzal malonate, 1-(3,4-dimethoxyphenyl)-4,4- dimethyl-1,3-pentanedione, 2-ethylhexyl dimethoxybenzylidene dioxoimidazolidine propionate, tetrahydroxybenzophenone, terephthalylidene dicamphor sulfonic acid, 2,4,6-tris[4-(2-ethylhexyloxycarbonyl)anilino]-1,3,5-triazine, methyl bis(trimethylsiloxy)silyl isopentyl trimethoxycinnamate, drometrizole trisiloxane, 2-ethylhexyl p-dimethylaminobenzoate, isopropyl p-methoxycinnamate, 2,4-bis-[{4-(2-ethylhexyloxy)-2-hydroxy}-phenyl]-6-(4-methoxyphenyl)-1,3,5-triazine, 2-hydroxy-4-methoxybenzophenone, hydroxymethoxybenzophenone sulfonic acid and its trihydrate, sodium hydroxymethoxybenzophenonesulfonate, phenylbenzimidazolesulfonic acid and 2,2'-methylenebis[6-(2H-benzotriazole-2-yl)-4-(1,1,3,3-tetramethylbutyl)phenol]. It is possible to use together a UVA absorber (e.g., hexyl diethylaminohydroxybenzoyl benzoate) and a UVB absorber (e.g., octocrylene) or an ultraviolet absorber of component (c)); any of these respective ultraviolet absorbers may be combined. When an ultraviolet absorber other than component (c) is included, the content thereof in the cosmetic is preferably from 0.1 to 10 wt %.

(6) Waxes (not Included in Component (f))

The waxes are not particularly limited, provided that they are ingredients which can be included in conventional cosmetics. Specific examples include silicone waxes, hydrocarbon waxes such as ceresin, ozokerite, paraffin, synthetic waxes, microcrystalline wax and polyethylene wax; vegetable waxes such as carnauba wax, rice wax, rice bran wax, jojoba wax (including extremely hydrogenated jojoba oil) and candelilla wax; and animal waxes such as spermaceti, beeswax and Snow White Wax. One, two or more of these waxes may be used. Silicone waxes that are used for the purpose of adjusting luster or the feel on use (examples of commercial products include KP-561P, 562P and KF-70205 from Shin-Etsu Chemical Co., Ltd.) are especially preferred. When a wax is included, the content thereof is preferably from 0.1 to 10% of the cosmetic.

(7) Other Additives

Examples of other additives include oil-soluble gelling agents, antiperspirants, humectants, antimicrobial agents and preservatives, fragrances, salts, antioxidants, pH adjustors, chelating agents, algefacients, skin beautifying ingredients (whitening agents, anti-inflammatory agents, cell activators, skin roughness improvers, circulation promoting ingredients, skin astringents, antiseborrheic agents, etc.), vitamins, amino acids, water-soluble polymeric compounds and plant extracts.

Oil-Soluble Gelling Agents

Examples of oil-soluble gelling agents include metal soaps such as aluminum stearate, magnesium stearate and zinc myristate; amino acid derivatives such as N-lauroyl-L-glutamic acid and α,γ-di-n-butylamine; dextrin fatty acid esters such as dextrin palmitate, dextrin stearate and dextrin 2-ethylhexanoate palmitate; sucrose fatty acid esters such as sucrose palmitate and sucrose stearate; fructooligosaccharide fatty acid esters such as fructooligosaccharide stearate and fructooligosaccharide 2-ethylhexanoate; benzilidene derivatives of sorbitol such as monobenzylidene sorbitol and dibenzylidene sorbitol; and organic-modified clay minerals such as disteardimonium hectorite, stearalkonium hectorite and hectorite.

Skin Beautifying Ingredients

Examples of skin beautifying ingredients include whitening agents such as arbutin, ascorbic acid and derivatives thereof; anti-inflammatory agents such as glycyrrhizates; and circulation-promoting ingredients such as benzyl nicotinate.

[Production Method]

The cosmetic of the invention can be produced by a known method. The method of incorporating component (a) is not particularly limited. Component (a) may be premixed with an oil such as component (b), component (c), or both components (b) and (c), or it may be emulsified beforehand in water and used as an emulsion. Alternatively, component (a) may be dispersed in a cosmetic that was prepared with all of the ingredients except for component (a), or it may be hydrophilized and used in a state that allows it to be easily added to an aqueous system. Of these, from the standpoint of the feel on use and the ease of producing the cosmetic, the method of premixing component (a) with component (b) is most preferred.

[Cosmetic]

The cosmetic of the invention may be in the form of an emulsified composition or a nonaqueous composition. When the desire is to impart a fresh feel on use, an emulsified composition is selected. The emulsified form may be any of the following: an oil-in-water (O/W) emulsion, water-in-oil (W/O) emulsion or oil-in-oil (O/O) emulsion. When the desire is to obtain an oily feel, water resistance or a powdery feel, a nonaqueous composition or powder form can be selected. In either of these cases, a good cosmetic can be obtained. In this invention, "nonaqueous composition" refers to an oil-based composition which contains substantially no water. The cosmetic of the invention is useful as a long-wear cosmetic because it has an excellent transfer resistance and durability. "Long-wear" means to prevent a cosmetic that has been applied to the skin from undergoing large changes from the freshly applied state due to sebum, sweat and the like, and to prevent the cosmetic from coming off due to rubbing, adhesion, etc.

The cosmetic of the invention may be used in a variety of products, including beauty essences, milky lotions, creams, hair care products, foundations, makeup bases, BB creams, concealers, sunscreens, loose powders, cheek colors, lipsticks, eye shadows, eye liners, body makeups and deodorants. In particular, in terms of being able to exhibit the advantageous effects of the invention, makeup cosmetics are preferred. Specifically, foundations, makeup bases, sunscreens, BB creams, concealers, cheek colors, and formulations that impart a sunscreening ability to these are preferred. The form of the cosmetic of the invention may be selected from among various forms, including liquids, creams, solids, pastes, gels, mousses, sprays, clays and powders.

EXAMPLES

The invention is illustrated more fully below by way of Examples and Comparative Examples, although the invention is not limited by these Examples. In these Examples, unless noted otherwise, references to "%" in a composition signify percent by weight and "ratio" refers to a weight ratio.

Examples, Comparative Examples

Cosmetics formulated as shown in the tables below were prepared by the method described below, and evaluations of the properties indicated below were carried out.

Preparation of Cosmetic: Examples 1 to 12, Comparative Examples 1 to 7

A: Component (2) was uniformly mixed on a three-roll mill.
B: A was added to component (1) and uniform mixture was carried out, giving a nonaqueous foundation.

Preparation of Cosmetic: Examples 13 to 19, Comparative Examples 8 to 11

A: Component (2) was uniformly mixed with a disperser.
B: A was added to component (1) and uniform mixture was carried out.
C: Component (3) was added to B and emulsification was carried out, giving an oil-in-water foundation.

(1) Evaluation of Properties

The cosmetics in the Examples and Comparative Examples were evaluated for transfer resistance of the cosmetic (lack of adhesion to the tissue when wiped with a tissue 20 minutes after application,), durability (the condition of the cosmetic three hours after application), feel on use (absence of stickiness), ease of application (spreadability) and finish (lack of white masking, powderiness and excessive dryness) by ten expert panelists. Evaluations were carried out based on the evaluation criteria shown in Table 1, and those evaluation were then rated according to the criteria shown below based on the average values for the ten panelists. The ratings thus obtained are presented in the tables below.

TABLE 1

| Item evaluated | Transfer resistance | Durability | Feel on use | Ease of application | Finish |
|---|---|---|---|---|---|
| 5 points | good | good | good | good | good |
| 4 points | somewhat good | somewhat good | somewhat good | somewhat good | somewhat good |
| 3 points | ordinary | ordinary | ordinary | ordinary | ordinary |
| 2 points | somewhat poor | somewhat poor | somewhat poor | somewhat poor | somewhat poor |
| 1 point | poor | poor | poor | poor | poor |

(2) Rating Criteria

⊙: Average score was 4.5 points or more
○: Average score was at least 3.5 points but less than 4.5 points
Δ: Average score was at least 2.5 points but less than 3.5 points
X: Average score was at least 1.5 points but less than 2.5 points
XX: Average score was less than 1.5 points
Ratings of "Δ" or better were regarded as acceptable.

TABLE 2

| | Composition (%) | Example 1 | 2 | 3 | 4 | 5 | 6 | 7 |
|---|---|---|---|---|---|---|---|---|
| (1) | (a) Silicone composite powder A [1)] | 10 | | | | 10 | | |
| | (a) Silicone composite powder B [2)] | | 10 | | | | 10 | |
| | (a) Silicone composite powder C [3)] | | | 10 | | | | 10 |
| | (a) Silicone composite powder D [4)] | | | | 10 | | | |
| | (d) Spherical polymethyl silsesquioxane [5)] | | | | | | 15 | |
| | (b) Decamethylcyclopentasiloxane [7)] | | 72 | 70 | 70 | 70 | 55 | 70 |
| | (b) Tristrimethylsiloxymethylsilane [8)] | 70 | | | | | | |
| (2) | (c) Dimethylpolysiloxane (6 cs) | 10 | 8 | | | | 10 | 6 |
| | (c) Triethylhexanoin (30 cs) | | | 10 | | 10 | | |
| | (c) Methylphenylpolysiloxane (15 cs) [9)] | | | | 10 | | | |
| | (f) Petrolatum | | | | | | | 4 |
| | (d) Silicone-treated titanium dioxide [10)] | 8.5 | 8.5 | 8.5 | 8.5 | 8.5 | 8.5 | 8.5 |
| | (d) Silicone-treated iron oxide [11)] | 1.5 | 1.5 | 1.5 | 1.5 | 1.5 | 1.5 | 1.5 |
| Total | | 100 | 100 | 100 | 100 | 100 | 100 | 100 |
| Content of (a) | | 10 | 10 | 10 | 10 | 10 | 10 | 10 |
| Content of (b) | | 70 | 72 | 70 | 70 | 70 | 55 | 70 |
| Content of (c) | | 10 | 8 | 10 | 10 | 10 | 10 | 6 |
| Content of (d) | | 10 | 10 | 10 | 10 | 10 | 25 | 10 |
| (a)/(c) | | 1.00 | 1.25 | 1.00 | 1.00 | 1.00 | 1.00 | 1.67 |
| (a)/(b) | | 0.14 | 0.14 | 0.14 | 0.14 | 0.14 | 0.18 | 0.14 |
| (a) + (d) | | 20 | 20 | 20 | 20 | 20 | 35 | 20 |
| (a)/(d) | | 1.0 | 1.0 | 1.0 | 1.0 | 1.0 | 0.4 | 1.0 |
| Evaluation of properties | Transfer resistance | ⊙ | ⊙ | ⊙ | ○ | Δ | ⊙ | Δ |
| | Durability | ○ | ⊙ | ○ | ○ | ○ | ○ | Δ |
| | Feel on use | ⊙ | ⊙ | ⊙ | ⊙ | ⊙ | ⊙ | ⊙ |
| | Ease of application | ○ | ⊙ | ⊙ | ⊙ | ⊙ | ○ | ○ |
| | Finish | ⊙ | ○ | ⊙ | ⊙ | ⊙ | Δ | ⊙ |

TABLE 3

|  | Composition (%) | Example 8 | Example 9 | Example 10 | Example 11 | Example 12 |
|---|---|---|---|---|---|---|
| (1) | (a) Silicone composite powder A [1) | 5 | 10 | 12 | 15 | 19 |
|  | (b) Decamethylcyclopentasiloxane [7) | 75 | 70 | 68 | 65 | 61 |
| (2) | (c) Dimethylpolysiloxane (6 cs) | 10 | 10 | 10 | 10 | 10 |
|  | (d) Silicone-treated titanium dioxide [10) | 8.5 | 8.5 | 8.5 | 8.5 | 8.5 |
|  | (d) Silicone-treated iron oxide [11) | 1.5 | 1.5 | 1.5 | 1.5 | 1.5 |
| Total |  | 100 | 100 | 100 | 100 | 100 |
| Content of (a) |  | 5 | 10 | 12 | 15 | 19 |
| Content of (b) |  | 75 | 70 | 68 | 65 | 61 |
| Content of (c) |  | 10 | 10 | 10 | 10 | 10 |
| Content of (d) |  | 10 | 10 | 10 | 10 | 10 |
| (a)/(c) |  | 0.50 | 1.00 | 1.20 | 1.50 | 1.90 |
| (a)/(b) |  | 0.07 | 0.14 | 0.18 | 0.23 | 0.31 |
| (a) + (d) |  | 15 | 20 | 22 | 25 | 29 |
| (a)/(d) |  | 0.5 | 1.0 | 1.2 | 1.5 | 1.9 |
| Evaluation of properties | Transfer resistance | △ | ⊚ | ⊚ | ⊚ | ⊚ |
|  | Durability | △ | ○ | ⊚ | ⊚ | ⊚ |
|  | Feel on use | ○ | ⊚ | ⊚ | ⊚ | ⊚ |
|  | Ease of application | ○ | ○ | ○ | ○ | △ |
|  | Finish | ⊚ | ⊚ | ○ | ○ | △ |

TABLE 4

|  | Composition (%) | Comparative Example 1 | 2 | 3 | 4 | 5 | 6 | 7 |
|---|---|---|---|---|---|---|---|---|
| (1) | (a) Silicone composite powder A [1) |  |  | 3.5 | 25 | 35 | 10 | 10 |
|  | (d) Spherical polymethyl silsesquioxane [5) | 10 |  |  |  |  |  |  |
|  | Partially crosslinked dimethylpolysiloxane (17.5%) - methyl trimethicone mixture [6) |  | 57.5 |  |  |  |  |  |
|  | (b) Decamethylcyclopentasiloxane [7) |  |  | 76.5 | 53 | 35 |  |  |
|  | (b) Tristrimethylsiloxymethylsilane [8) | 70 | 22.5 |  |  |  |  | 80 |
| (2) | (c) Dimethylpolysiloxane (6 cs) | 10 | 10 | 10 | 12 | 20 | 80 |  |
|  | (d) Silicone-treated titanium dioxide [10) | 8.5 | 8.5 | 8.5 | 8.5 | 8.5 | 8.5 | 8.5 |
|  | (d) Silicone-treated iron oxide [11) | 1.5 | 1.5 | 1.5 | 1.5 | 1.5 | 1.5 | 1.5 |
| Total |  | 100 | 100 | 100 | 100 | 100 | 100 | 100 |
| Content of (a) |  | 0 | 0 | 3.5 | 25 | 35 | 10 | 10 |
| Content of (b) |  | 70 | 22.5 | 76.5 | 53 | 35 | 0 | 80 |
| Content of (c) |  | 10 | 10 | 10 | 12 | 20 | 80 | 0 |
| Content of (d) |  | 20 | 10 | 10 | 10 | 10 | 10 | 10 |
| (a)/(c) |  | — | — | 0.35 | 2.08 | 1.75 | 0.13 | — |
| (a)/(b) |  | — | — | 0.05 | 0.47 | 1.00 | — | 0.13 |
| (a) + (d) |  | 20 | 10 | 13.5 | 35 | 45 | 20 | 20 |
| (a)/(d) |  | — | — | 0.4 | 2.5 | 3.5 | 1.0 | 1.0 |
| Evaluation of properties | Transfer resistance | X | X | △ | ⊚ | △ | XX | ⊚ |
|  | Durability | X | X | X | ○ | ○ | ○ | ○ |
|  | Feel on use | ○ | X | △ | ⊚ | ⊚ | ⊚ | ⊚ |
|  | Ease of application | ○ | △ | ○ | △ | △ | △ | ○ |
|  | Finish | ⊚ | ⊚ | ⊚ | X | X | ⊚ | XX |

The notes in Tables 2 to 4 are as follows.

1) (Vinyl dimethicone/methicone silsesquioxane) crosspolymer:
   KSP-100 (average particle size, 5 μm), from Shin-Etsu Chemical Co., Ltd.; oil absorption, 112 mL/100 g 2) (Vinyl dimethicone/methicone silsesquioxane) crosspolymer:
   KSP-101 (average particle size, 12 μm), from Shin-Etsu Chemical Co., Ltd.; oil absorption, 121 mL/100 g 3) Polysilicone-22:
   KSP-441 (average particle size, 12 μm), from Shin-Etsu Chemical Co., Ltd.; oil absorption, 126 mL/100 g 4) Diphenyl dimethicone/vinyl diphenyl dimethicone/silsesquioxane) crosspolymer:
   KSP-300 (average particle size, 5 μm), from Shin-Etsu Chemical Co., Ltd.; oil absorption, 140 mL/100 g 5) KMP-591 (oil non-absorbent powder; particle size, 5 μm), from Shin-Etsu Chemical Co., Ltd.; oil absorption, 42 mL/100 g 6) KSG-1610 (crosslinked compound, 17.5%; methyl trimethicone, 82.5%), from Shin-Etsu Chemical Co., Ltd.

7) KF-995 (Shin-Etsu Chemical Co., Ltd.)

8) TMF-1.5 (Shin-Etsu Chemical Co., Ltd.)

9) KF-56A (Shin-Etsu Chemical Co., Ltd.)

10) KTP-09W (Shin-Etsu Chemical Co., Ltd.; oil absorption, 12 mL/100 g)
11) KTP-09R, Y and B (mixture from Shin-Etsu Chemical Co., Ltd.; oil absorption, 12 mL/100 g)

The contents are the amounts included in the formulated products shown in the tables, with the amounts of components (a) to (d) and also (a)/(b), (a)/(c) and (a)/(d) being indicated based on the amount of pure constituent (the same applies below).

TABLE 5

|   | Composition (%) | | 13 | 14 | 15 | 16 | 17 | 18 | 19 |
|---|---|---|---|---|---|---|---|---|---|
| (1) | (a) Silicone composite powder A [1)] | | 5 | | 5 | | | 10 | 14 |
| | (a) Silicone composite powder C [2)] | | | 5 | | 5 | 10 | | |
| | Partially branched polyether-modified silicone (20%) - cyclopentasiloxane mixture [3)] | | 4 | 4 | 4 | 4 | 4 | 4 | 4 |
| | Partially branched dimethylpolysiloxane (7%) - cyclopentasiloxane mixture [4)] | | 3 | 3 | 3 | 3 | 2 | | |
| | (b) Decamethylcyclopentasiloxane [5)] | | 22 | 22 | 22 | 22 | 18 | 15.4 | 11.8 |
| | Silicone-branched polyether-modified silicone [6)] | | 2 | 2 | 2 | 2 | 2 | 2 | 2 |
| | Organic-modified bentonite | | 0.8 | 0.8 | 0.8 | 0.8 | 0.8 | 0.4 | |
| (2) | (c) Neopentyl glycol diethylhexanoate (14 cs) | | 5 | 5 | 5 | 5 | 5 | 10 | 10 |
| | Silicone-branched polyglycerol-modified silicone [8)] | | 0.2 | 0.2 | 0.2 | 0.2 | 0.2 | 0.2 | 0.2 |
| | (d) Silicone-treated titanium dioxide [9)] | | 8.5 | 8.5 | 8.5 | 8.5 | 8.5 | 8.5 | 8.5 |
| | (d) Silicone-treated iron oxide [10)] | | 1.5 | 1.5 | 1.5 | 1.5 | 1.5 | 1.5 | 1.5 |
| (3) | Ethanol | | 7 | 7 | | 3 | 7 | 7 | 7 |
| | (e) Butylene glycol | | | | 7 | 4 | | | |
| | Sodium chloride | | 0.5 | 0.5 | 0.5 | 0.5 | 0.5 | 0.5 | 0.5 |
| | Sodium citrate | | 0.2 | 0.2 | 0.2 | 0.2 | 0.2 | 0.2 | 0.2 |
| | Water | | 40.3 | 40.3 | 40.3 | 40.3 | 40.3 | 40.3 | 40.3 |
| | Total | | 100 | 100 | 100 | 100 | 100 | 100 | 100 |
| | Content of (a) | | 5 | 5 | 5 | 5 | 10 | 10 | 14 |
| | Content of (b) | | 27.99 | 27.99 | 27.99 | 27.99 | 23.06 | 18.6 | 15 |
| | Content of (c) | | 5 | 5 | 5 | 5 | 5 | 10 | 10 |
| | Content of (d) | | 10 | 10 | 10 | 10 | 10 | 10 | 10 |
| | (a)/(c) | | 1.00 | 1.00 | 1.00 | 1.00 | 2.00 | 1.00 | 1.40 |
| | (a)/(b) | | 0.18 | 0.18 | 0.18 | 0.18 | 0.43 | 0.54 | 0.93 |
| | (a) + (d) | | 15 | 15 | 15 | 15 | 20 | 20 | 24 |
| | (a)/(d) | | 0.5 | 0.5 | 0.5 | 0.5 | 1.0 | 1.0 | 1.4 |
| | Evaluation of properties | Transfer resistance | ◎ | ◎ | Δ | Δ | ◎ | ○ | Δ |
| | | Durability | ◎ | ◎ | ○ | ◎ | ◎ | ○ | Δ |
| | | Feel on use | ◎ | ◎ | ◎ | ◎ | ◎ | ○ | ○ |
| | | Ease of application | ○ | ◎ | ◎ | ◎ | ○ | ○ | Δ |
| | | Finish | ○ | ◎ | ◎ | ◎ | ○ | ◎ | Δ |

TABLE 6

|   | Composition (%) | | 8 | 9 | 10 | 11 |
|---|---|---|---|---|---|---|
| (1) | (a) Silicone composite powder A [1)] | | | | 7 | 5 |
| | (a) Silicone composite powder C [2)] | | | 5 | | |
| | Partially branched polyether-modified silicone (20%) - cyclopentasiloxane mixture [3)] | | 4 | 4 | 4 | 4 |
| | Partially branched dimethylpolysiloxane (7%) - cyclopentasiloxane mixture [4)] | | 3 | 3 | 3 | 3 |
| | (b) Decamethylcyclopentasiloxane [5)] | | 27 | 11 | 22 | 22 |
| | Silicone-branched polyether-modified silicone [6)] | | 2 | 2 | 2 | 2 |
| | Organic-modified bentonite | | 0.8 | 0.8 | 0.8 | 0.8 |
| | Acrylic silicone (40%) cyclopentasiloxane mixture [7)] | | 2 | | | |
| (2) | (c) Neopentyl glycol diethylhexanoate (14 cs) | | 3 | 16 | 3 | |
| | Ethylhexyl hydroxystearate (105 cs) | | | | | 5 |
| | Silicone-branched polyglycerol-modified silicone [8)] | | 0.2 | 0.2 | 0.2 | 0.2 |
| | (d) Silicone-treated titanium dioxide [9)] | | 8.5 | 8.5 | 8.5 | 8.5 |
| | (d) Silicone-treated iron oxide [10)] | | 1.5 | 1.5 | 1.5 | 1.5 |
| (3) | Ethanol | | 7 | 7 | 7 | 7 |
| | Sodium chloride | | 0.5 | 0.5 | 0.5 | 0.5 |
| | Sodium citrate | | 0.2 | 0.2 | 0.2 | 0.2 |
| | Water | | 40.3 | 40.3 | 40.3 | 40.3 |
| | Total | | 100 | 100 | 100 | 100 |
| | Content of (a) | | 0 | 5 | 7 | 5 |
| | Content of (b) | | 29.51 | 14.63 | 24.86 | 24.86 |
| | Content of (c) | | 3 | 16 | 3 | 0 |
| | Content of (d) | | 10 | 10 | 10 | 10 |

TABLE 6-continued

|  | Composition (%) | Comparative Example | | | |
|---|---|---|---|---|---|
|  |  | 8 | 9 | 10 | 11 |
| (a)/(c) |  | — | 0.31 | 2.33 | — |
| (a)/(b) |  | — | 0.34 | 0.28 | 0.20 |
| (a) + (d) |  | 10 | 15 | 17 | 15 |
| (a)/(d) |  | — | 0.5 | 0.7 | 0.5 |
| Evaluation of properties | Transfer resistance | Δ | ○ | ◎ | XX |
|  | Durability | X | X | ○ | X |
|  | Feel on use | Δ | Δ | Δ | ○ |
|  | Ease of application | Δ | ○ | Δ | Δ |
|  | Finish | ◎ | ◎ | X | ○ |

The notes in Tables 5 and 6 are as follows.

1) (Vinyl dimethicone/methicone silsesquioxane) crosspolymer:
   KSP-100 (average particle size, 5 μm),
   from Shin-Etsu Chemical Co., Ltd.; oil absorption, 112 mL/100 g
2) Polysilicone-22:
   KSP-441 (average particle size, 12 μm),
   from Shin-Etsu Chemical Co., Ltd.; oil absorption, 126 mL/100 g
3) KSG-240 (crosslinked compound, 20%; decamethylcyclopentasiloxane, 80%), from Shin-Etsu Chemical Co., Ltd.
4) KSG-15 (crosslinked compound, 7%; decamethylcyclopentasiloxane, 93%), from Shin-Etsu Chemical Co., Ltd.
5) KF-995 (Shin-Etsu Chemical Co., Ltd.)
6) KF-6028 (Shin-Etsu Chemical Co., Ltd.)
7) KP-545 (solids content, 40%; decamethylcyclopentasiloxane, 60%),
   from Shin-Etsu Chemical Co., Ltd.
8) KF-6106 (Shin-Etsu Chemical Co., Ltd.)
9) KTP-09W (Shin-Etsu Chemical Co., Ltd.; oil absorption, 12 mL/100 g)
10) KTP-09R, Y and B
    (mixture from Shin-Etsu Chemical Co., Ltd.; oil absorption, 12 mL/100 g)

From Tables 2 to 6, it is apparent that the cosmetics in the Examples had a transfer resistance (lack of adhesion to tissue), durability (condition following one hour of exercise after applying cosmetic), feel on use (absence of stickiness), ease of application (spreadability) and finish (lack of white masking, powderiness and excessive dryness) that were excellent. In Comparative Examples 1 and 2 which did not include component (a), a sufficient transfer resistance and durability were not obtained. In Comparative Example 8, a sufficient durability was not obtained. In Comparative Examples 3 and 9 in which (a)/(c) was less than 0.37, sufficient durability was not obtained. Powderiness was strongly sensed in Comparative Examples 4 and 10 wherein (a)/(c) was larger than 2.0, in Comparative Example 5 wherein the content of component (a) exceeded 30 wt %, and in Comparative Example 7 wherein component (c) was not included. In Comparative Example 6 which did not include component (b), transfer resistance was not obtained. In Comparative Example 1 in which a nonvolatile oil having a viscosity of 105 mm2/s (ethylhexyl hydroxystearate) was used instead of component (c), sufficient transfer resistance and durability were not obtained.

In the following Examples, the ingredients are indicated using primarily the INCI names.

Example 20

Oil Foundation

<Preparation of Cosmetic>

A: Ingredients 1 to 4 were uniformly mixed.
B: Ingredients 12 to 17 were uniformly mixed on a roll mill.
C: Ingredients 5 to 11 were added to A and uniformly mixed.
D: B was added to C and uniformly mixed, giving an oil foundation.

| Composition | % |
|---|---|
| 1. Silicone composite powder[1] | 8 |
| 2. Isododecane | 5 |
| 3. Cyclopentasiloxane | balance |
| 4. Dimethicone (2 cs) | 30 |
| 5. Ethanol | 6 |
| 6. Silicone/alkyl-branched polyether-modified silicone[2] | 2 |
| 7. Acrylic silicone (40%) - cyclopentasiloxane mixture[3] | 1.5 |
| 8. Trimethylsiloxysilicic acid (50%) - cyclopentasiloxane mixture[4] | 1 |
| 9. Organic-modified bentonite | 1.5 |
| 10. Hydrophobic anhydrous silica[5] | 1 |
| 11. Ethylhexyl methoxycinnamate | 3 |
| 12. Silicone-branched polyglycerol-modified silicone[6] | 1 |
| 13. Metal soap-treated microparticulate titanium dioxide | 5 |
| 14. Diphenylsiloxy phenyl trimethicone[7] | 3 |
| 15. Triethylhexanoin | 3 |
| 16. Silicone-modified titanium dioxide[8] | 8.5 |
| 17. Silicone-modified iron oxide[8] | 1.5 |
| Total | 100.0 |

Content of (a): 14.0%
(a)/(c): 1.56
[1] KSP-411 (Shin-Etsu Chemical Co., Ltd.)
[2] KF-6038 (Shin-Etsu Chemical Co., Ltd.)
[3] KF-545 (Shin-Etsu Chemical Co., Ltd.)
[4] KF-9021 (Shin-Etsu Chemical Co., Ltd.)
[5] AEROSIL R972 (Nippon Aerosil Co., Ltd.)
[6] KF-6106 (Shin-Etsu Chemical Co., Ltd.)
[7] KF-56A (Shin-Etsu Chemical Co., Ltd.)
[8] The powder was hydrophobized by surface treatment using KF-9901 (Shin-Etsu Chemical Co., Ltd.)

The resulting oil foundation was confirmed to have an excellent transfer resistance, durability, feel on use, ease of application and finish.

Example 21

Solid Foundation

<Preparation of Cosmetic>

A: Ingredients 7 to 12 were uniformly mixed on a roll mill.
B: Ingredients 1 to 6 were uniformly mixed at 85° C.
C: A was added to B and uniformly mixed, then filled into a mold at 80° C., giving a solid foundation.

| Composition | % |
| --- | --- |
| 1. Silicone composite powder[1] | 10 |
| 2. Cyclopentasiloxane | balance |
| 3. Polymethyl silsesquioxane[2] | 4 |
| 4. Squalane | 1.5 |
| 5. Silicone/alkyl-branched polyether-modified silicone[3] | 0.5 |
| 6. Ceresin | 8.5 |
| 7. Partially crosslinked dimethylpolysiloxane composition[4] | 6 |
| 8. Diphenylsiloxy phenyl trimethicone[5] | 3 |
| 9. Silicone/alkyl-branched polyglycerol-modified silicone[6] | 1 |
| 10. Alkylsilane-treated titanium dioxide[7] | 8.5 |
| 11. Alkylsilane-treated iron oxide[7] | 1.5 |
| 12. Silicone-treated microparticulate zinc oxide | 8 |
| Total | 100.0 |

Content of (a): 18.0%
(a)/(c): 1.88
[1]KSP-101 (Shin-Etsu Chemical Co., Ltd.)
[2]KMP-590 (Shin-Etsu Chemical Co., Ltd.)
[3]KF-6038 (Shin-Etsu Chemical Co., Ltd.)
[4]KSG-19 (crosslinked compound, 15%; dimethylpolysiloxane (6 cs), 85%), from Shin-Etsu Chemical Co., Ltd.
[5]KF-56A (Shin-Etsu Chemical Co., Ltd.)
[6]KF-6105 (Shin-Etsu Chemical Co., Ltd.)
[7]The powder was hydrophobized by surface treatment using AES-3083 (Shin-Etsu Chemical Co., Ltd.)

The resulting solid foundation was confirmed to have an excellent transfer resistance, durability, feel on use, ease of application and finish.

Example 22

Water-in-Oil (W/O) Makeup Base
<Preparation of Cosmetic>
A: Ingredients 6 to 10 were uniformly mixed on a roll mill.
B: Ingredients 11 to 16 were uniformly mixed.
C: Ingredients 1 to 5 were added to A and uniformly mixed.
D: B was added to C and uniformly mixed, giving a water-in-oil makeup base.

| Composition | % |
| --- | --- |
| 1. Silicone composite powder[1] | 8.5 |
| 2. Methyl trimethicone[2] | 35 |
| 3. Ethylhexyl methoxycinnamate | 7 |
| 4. Hexyl diethylaminohydroxybenzoyl benzoate | 2 |
| 5. Alkyl-modified partially crosslinked dimethylpolysiloxane composition[3] | 10 |
| 6. Silicone/alkyl-branched polyether-modified silicone[4] | 2 |
| 7. Diphenylsiloxy phenyl trimethicone[5] | 1 |
| 8. Organic-modified bentonite | 0.2 |
| 9. Silicone-treated titanium dioxide[6] | 2 |
| 10. Silicone-treated iron oxide[7] | 0.5 |
| 11. Sodium chloride | 0.5 |
| 12. Sodium citrate | 0.2 |
| 13. Ethanol | 6 |
| 14. Trehalose | 3 |
| 15. Ethylhexylglycerin | 0.1 |
| 16. Water | balance |
| Total | 100.0 |

Content of (a): 8.5%
(a)/(c): 1.06
[1]KSP-300 (Shin-Etsu Chemical Co., Ltd.)
[2]TMF-1.5 (Shin-Etsu Chemical Co., Ltd.)
[3]KSG-42A (crosslinked compound, 20%; isododecane, 80%), from Shin-Etsu Chemical Co., Ltd.
[4]KF-6038 (Shin-Etsu Chemical Co., Ltd.)
[5]KF-56A (Shin-Etsu Chemical Co., Ltd.)
[6]KTP-09W (Shin-Etsu Chemical Co., Ltd.)
[7]KTP-09R (Shin-Etsu Chemical Co., Ltd.)

The resulting water-in-oil makeup base was confirmed to have an excellent ease of application and finish. When foundation was applied over the makeup base, the transfer resistance and durability were confirmed to be excellent.

Example 23

Water-in-Oil (W/O) Makeup Base
<Preparation of Cosmetic>
A: Ingredients 1 to 8 were added together and uniformly mixed on a roll mill.
B: Ingredients 9 to 14 were uniformly mixed.
C: B was added to A and uniformly mixed, giving a water-in-oil makeup base.

| Composition | % |
| --- | --- |
| 1. Silicone composite powder[1] | 8 |
| 2. Dimethicone (2 cs) | 15 |
| 3. Metal soap-treated microparticulate titanium dioxide dispersion[2] | 5 |
| 4. Silicone-treated microparticulate zinc oxide dispersion[3] | 10 |
| 5. Silicone/alkyl-modified partially crosslinked dimethylpolysiloxane composition[4] | 6 |
| 6. Silicone/alkyl-branched polyglycerol-modified silicone[5] | 2 |
| 7. Silicone/alkyl-branched crosslinked polyglycerol-modified silicone[6] | 2 |
| 8. Isononyl isononanoate | 8 |
| 9. Sodium chloride | 0.5 |
| 10. Sodium citrate | 0.2 |
| 11. Pentylene glycol | 2 |
| 12. PEG-32 | 3 |
| 13. Phenoxyethanol | 0.2 |
| 14. Water | balance |
| Total | 100.0 |

Content of (a): 16.0%
(a)/(c): 2.00
[1]KSP-441 (Shin-Etsu Chemical Co., Ltd.)
[2]SPD-T5 (powder, 40%), from Shin-Etsu Chemical Co., Ltd.
[3]SPD-Z5 (powder, 60%), from Shin-Etsu Chemical Co., Ltd.
[4]KSG-045Z (crosslinked compound, 20%; cyclopentasiloxane, 80%) (Shin-Etsu Chemical Co., Ltd.)
[5]KF-6105 (Shin-Etsu Chemical Co., Ltd.)
[6]KSG-850Z (crosslinked compound, 25%; cyclopentasiloxane, 75%) from Shin-Etsu Chemical Co., Ltd.

The resulting water-in-oil makeup base was confirmed to have an excellent ease of application and finish. When foundation was applied over the makeup base, the transfer resistance and durability were confirmed to be excellent.

Example 24

Cast Point Makeup
<Preparation of Cosmetic>
A: Ingredients 11 to 16 were uniformly mixed on a roll mill.
B: Ingredients 1 to 10 were uniformly mixed at 95° C.
C: A was added to B and uniformly mixed, then filled into a mold at 80° C., giving a cast point makeup.

| Composition | % |
| --- | --- |
| 1. Silicone composite powder[1] | 6 |
| 2. Phenyl-modified silicone composite powder[2] | 4 |
| 3. Cyclopentasiloxane | balance |
| 4. Silicone/alkyl-branched polyglycerol-modified silicone[3] | 1 |
| 5. Silicone wax[4] | 20 |
| 6. Candelilla wax | 3 |
| 7. Polyethylene | 5 |
| 8. Diphenylsiloxy phenyl trimethicone[5] | 15 |
| 9. Triethylhexanoin | 4 |
| 10. Hydrogenated polyisobutene (800 mm$^2$/s) | 4.5 |
| 11. Polyglyceryl triisostearate | 4 |
| 12. Sericite | 1.6 |

-continued

| Composition | | % |
|---|---|---|
| 13. | Red No. 202 | 0.3 |
| 14. | Red No. 201 | 0.1 |
| 15. | Yellow No. 4 | 1 |
| 16. | Silicone-treated titanium dioxide[6] | 2 |
| | Total | 100.0 |

Content of (a): 10.0%
(a)/(c): 0.53
[1] KSP-105 (Shin-Etsu Chemical Co., Ltd.)
[2] KSP-300 (Shin-Etsu Chemical Co., Ltd.)
[3] KF-6105 (Shin-Etsu Chemical Co., Ltd.)
[4] KP-561P (Shin-Etsu Chemical Co., Ltd.)
[5] KTP-09W (Shin-Etsu Chemical Co., Ltd.)

The resulting cast point makeup was confirmed to have an excellent transfer resistance, durability, feel on use, ease of application and finish.

Example 25

Mousse Foundation
<Preparation of Cosmetic>
A: Ingredients 1 to 5 were uniformly mixed.
B: Ingredients 6 to 14 were uniformly mixed on a roll mill.
C: B was added to A and uniformly mixed, giving a mousse foundation.

| Composition | | % |
|---|---|---|
| 1. | Alkyl-modified silicone composite powder[1] | 11 |
| 2. | Phenyl-modified silicone composite powder[2] | 4.5 |
| 3. | Silicone/alkyl-modified partially crosslinked dimethylpolysiloxane composition[3] | 33 |
| 4. | Trimethylsiloxysilicic acid (50%) - cyclopentasiloxane mixture[4] | 11 |
| 5. | Dimethicone (2 cs) | balance |
| 6. | Diphenylsiloxy phenyl trimethicone[5] | 5 |
| 7. | Squalane | 2 |
| 8. | Jojoba oil | 1 |
| 9. | Spherical polymethyl methacrylate (8 μm) | 2 |
| 10. | Silicone-treated titanium dioxide[6] | 6 |
| 11. | Silicone-treated iron oxide[6] | 1.4 |
| 12. | Metal soap-treated microparticulate titanium dioxide | 9 |
| 13. | Silicone-treated talc[6] | 3 |
| 14. | Silicone-treated mica[6] | 1.1 |
| | Total | 100.0 |

Content of (a): 15.5%
(a)/(c): 1.94
[1] KSP-441 (Shin-Etsu Chemical Co., Ltd.)
[2] KSP-300 (Shin-Etsu Chemical Co., Ltd.)
[3] KSG-048Z (crosslinked compound, 20%; dimethicone (2 cs), 80%), from Shin-Etsu Chemical Co., Ltd.
[4] KF-7312L (Shin-Etsu Chemical Co., Ltd.)
[5] KF-56A (Shin-Etsu Chemical Co., Ltd.)
[6] The powder was hydrobized by surface treatment using KF-9909 (Shin-Etsu Chemical Co., Ltd.)

The resulting mousse foundation was confirmed to have an excellent transfer resistance, durability, feel on use, ease of application and finish.

Example 26

Oil-in-Water (01W) Makeup Base
<Preparation of Cosmetic>
A: Ingredients 1 to 3 were added together and uniformly mixed.
B: Ingredients 4 to 9 were uniformly mixed at 85° C. and cooled.
C: B was added to A and uniformly mixed, giving an oil-in-water makeup base.

| Composition | | % |
|---|---|---|
| 1. | Silicone composite powder[1] | 8 |
| 2. | Cyclopentasiloxane | 20 |
| 3. | Dimethicone (6 cs) | 10 |
| 4. | Polysorbate-60 | 2 |
| 5. | BG | 5 |
| 6. | Acrylamide composition[2] | 2.5 |
| 7. | Ethanol | 10 |
| 8. | Xanthan gum | 0.2 |
| 9. | Water | balance |
| | Total | 100.0 |

Content of (a): 8.0%
(a)/(c): 0.80
[1] KSP-441 (Shin-Etsu Chemical Co., Ltd.)
[2] Sepigel 305 (from SEPPIC)

The resulting oil-in-water makeup base was confirmed to have an excellent feel on use, ease of application and finish. When foundation was applied over the makeup base, the transfer resistance and durability were confirmed to be excellent.

Example 27

Water-in-Oil (W/O) Makeup Base
<Preparation of Cosmetic>
A: Ingredients 2 to 5 were added together and uniformly mixed.
B: Ingredients 6 to 11 were uniformly mixed.
C: B was emulsified in A, and Ingredient 1 was added and uniformly mixed, giving a water-in-oil makeup base.

| Composition | | % |
|---|---|---|
| 1. | Silicone composite powder[1] | 5 |
| 2. | Cyclopentasiloxane | 12 |
| 3. | Partially crosslinked polyether-modified silicone[2] | 3 |
| 4. | Partially crosslinked dimethylpolysiloxane composition[3] | 1 |
| 5. | Polyether-modified silicone[4] | 0.2 |
| 6. | Magnesium sulfate | 1 |
| 7. | Sodium citrate | 0.2 |
| 8. | Ethanol | 8 |
| 9. | Glycerin | 3 |
| 10. | Phenoxyethanol | 0.3 |
| 11. | Water | balance |
| | Total | 100.0 |

Content of (a): 5.0%
(a)/(c): 1.61
[1] KSP-101 (Shin-Etsu Chemical Co., Ltd.)
[2] KSG-210 (crosslinked compound, 25%; dimethicone (6 cs), 75%), from Shin-Etsu Chemical Co., Ltd.
[3] KSG-19 (crosslinked compound, 15%; dimethicone (6 cs), 85%), from Shin-Etsu Chemical Co., Ltd.
[4] KF-6017 (Shin-Etsu Chemical Co., Ltd.)

The resulting water-in-oil makeup base was confirmed to have an excellent feel on use, ease of application and finish. When foundation was applied over the makeup base, the transfer resistance and durability were confirmed to be excellent.

The invention claimed is:
1. A cosmetic comprising
(a) a highly oil-absorbent powder having an oil absorption of at least 50 mL/100 g, which is one or more selected from the group consisting of, as defined in the International Nomenclature of Cosmetic Ingredient (INCI): (vinyl dimethicone/methicone silsesquioxane)

crosspolymer, (diphenyl dimethicone/vinyl diphenyl dimethicone/silsesquioxane) crosspolymer, polysilicone-22 and polysilicone-1 crosspolymer,
(b) a volatile oil, and
(c) a nonvolatile oil selected from silicone oils having a kinematic viscosity at 25° C. of from 5 to 100 mm$^2$/s, high-polarity oils having an inorganic-organic balance (IOB) of from 0.1 to 0.6 and a kinematic viscosity at 25° C. of at least 5 mm$^2$/s and less than 20 mm$^2$/s, and triethylhexanoin,
wherein the weight ratio in which components (a) and (c) are included, expressed as (a)/(c), is from 0.37 to 2.0.

2. The cosmetic of claim 1, wherein the oil absorption of component (a) is at least 70 mL/100 g.

3. The cosmetic of claim 1, further comprising (d) a powder other than component (a).

4. The cosmetic of claim 3, wherein the combined amount of components (a) and (d) is not more than 45 wt % of the cosmetic.

5. The cosmetic of claim 3, wherein the weight ratio in which components (a) and (d) are included, expressed as (a)/(d), is at least 0.3.

6. The cosmetic of claim 1, wherein component (a) is polysilicone-22 and component (c) is a nonvolatile oil that has a kinematic viscosity at 25° C. of from 5 to 100 mm$^2$/s and is selected from the group consisting of silicone oils, low-polarity oils and high-polarity oils.

7. The cosmetic of claim 1, wherein component (a) is selected from the group consisting of (vinyl dimethicone/methicone silsesquioxane) crosspolymer and polysilicone-1 crosspolymer, and component (c) is selected from silicone oils that have a kinematic viscosity at 25° C. of from 5 to 100 mm$^2$/s and high-polarity oils that have an IOB of from 0.1 to 0.6 and a kinematic viscosity at 25° C. of at least 5 mm$^2$/s and less than 20 mm$^2$/s.

8. The cosmetic of claim 1, wherein component (a) is (diphenyl dimethicone/vinyl diphenyl dimethicone/silsesquioxane) crosspolymer and component (c) is a nonvolatile oil that has a kinematic viscosity at 25° C. of from 5 to 100 mm$^2$/s and is selected from the group consisting of methylphenylpolysiloxane, high-polarity oils and ultraviolet absorbers.

9. The cosmetic of claim 1, further comprising (e) a water-soluble nonvolatile ingredient in an amount of less than 12 wt % of the cosmetic.

10. The cosmetic of claim 1, further comprising (f) a nonvolatile oil having a kinematic viscosity at 25° C. in excess of 100 mm$^2$/s in an amount of less than 5 wt % of the cosmetic.

11. The cosmetic of claim 1 which is a makeup cosmetic.

12. The cosmetic of claim 1, wherein the weight ratio in which components (a) and (c) are included, expressed as (a)/(c), is from 0.50 to 1.9.

13. The cosmetic of claim 1, wherein the amount of component (b) is 5 to 80 wt % of the cosmetic.

14. The cosmetic of claim 1, wherein the amount of component (a) is not more than 20 wt % of the cosmetic, and the amount of component (c) is not more than 10 wt % of the cosmetic.

* * * * *